United States Patent [19]

Nierman

[11] Patent Number: 4,880,015

[45] Date of Patent: Nov. 14, 1989

[54] BIOPSY FORCEPS

[76] Inventor: David M. Nierman, 250 E. 87th St., Apt. 30-G, New York, N.Y. 10128

[21] Appl. No.: 202,169

[22] Filed: Jun. 3, 1988

[51] Int. Cl.⁴ ............................................. A61B 10/00
[52] U.S. Cl. ..................... 128/751; 128/321; 30/199; 30/245
[58] Field of Search ............... 128/321, 322, 323, 324, 128/749, 751, 752; 30/199, 245

[56] References Cited

U.S. PATENT DOCUMENTS

| 4,646,751 | 3/1987 | Maslanka | 128/751 |
| 4,763,669 | 8/1988 | Jaeger | 128/751 |

Primary Examiner—Max Hindenburg
Assistant Examiner—Randy Citrin

[57] ABSTRACT

This invention relates to a biopsy forcep for use in a flexible fiberoptic bronchoscope. More particularly, this invention is directed to a biopsy forcep having an increased range of operability when used in conjunction with the flexible fiberoptic bronchoscope when obtaining tissue samples such as smooth growths in the trachea or main stem bronchii.

24 Claims, 7 Drawing Sheets

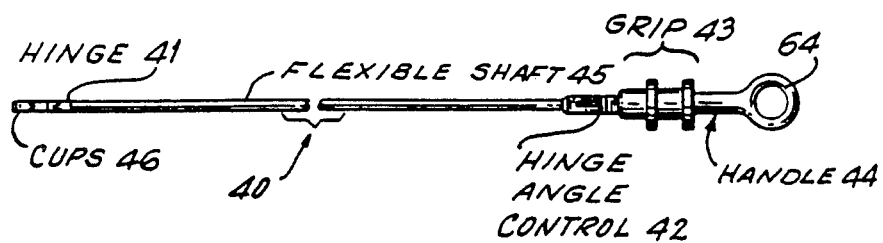
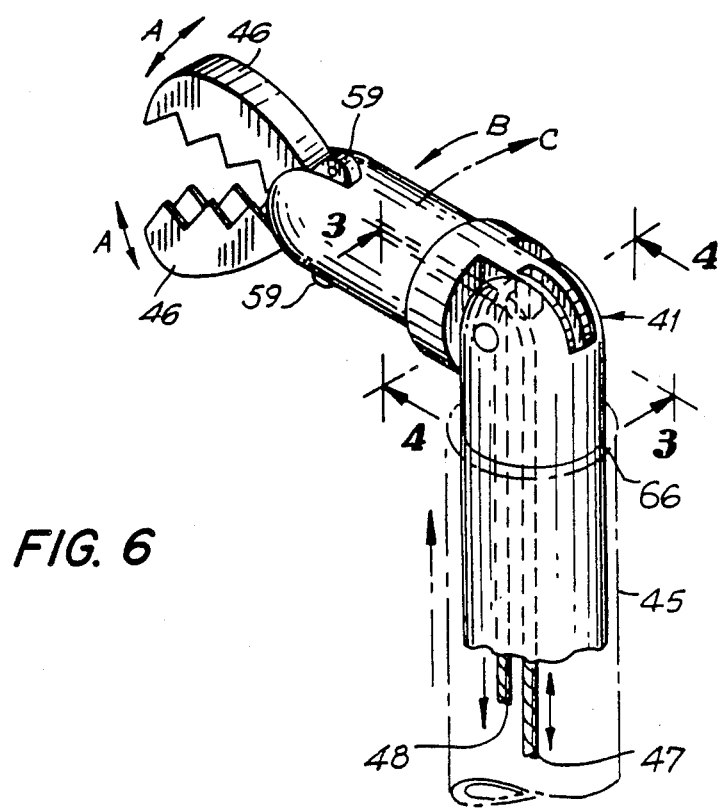

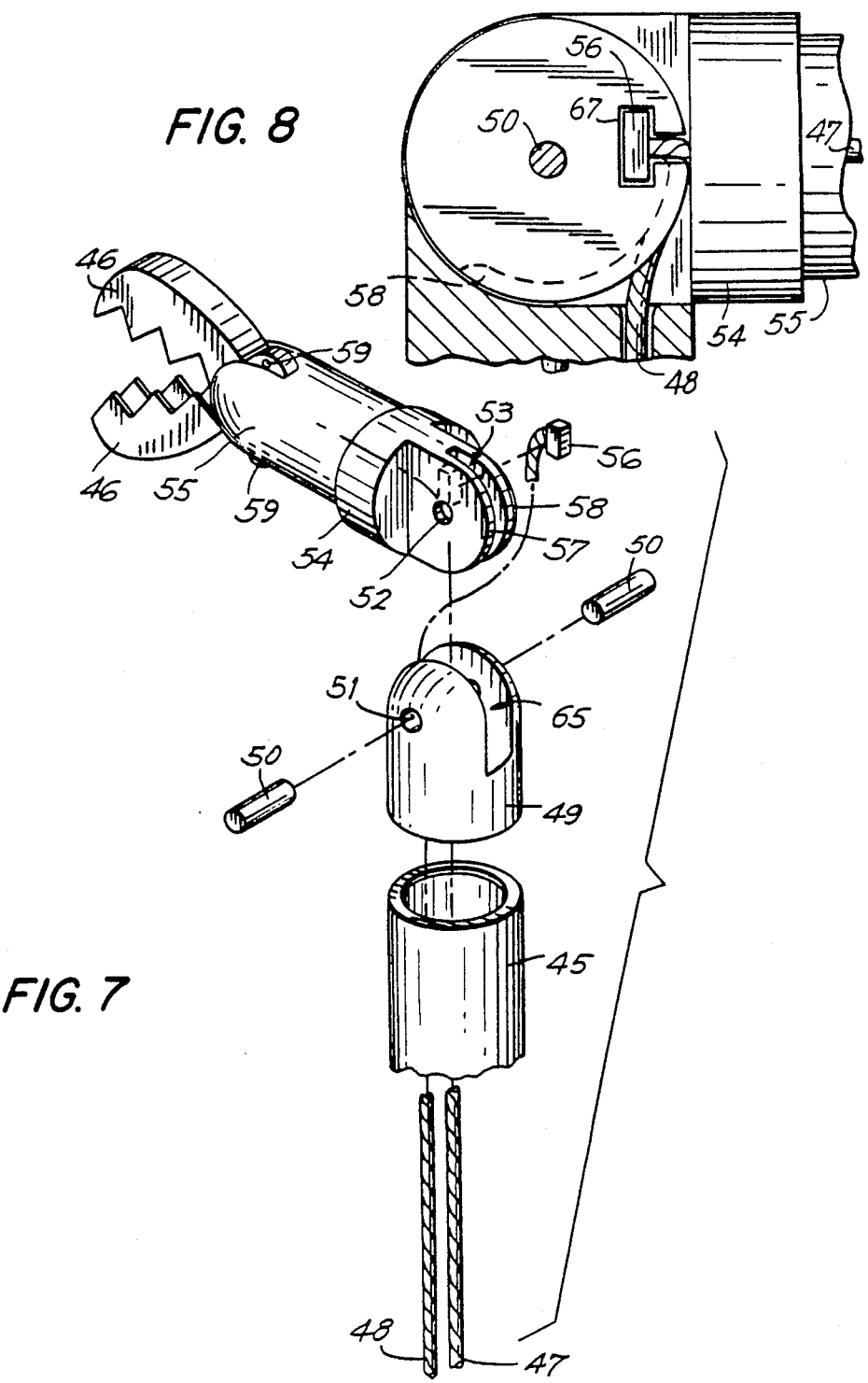

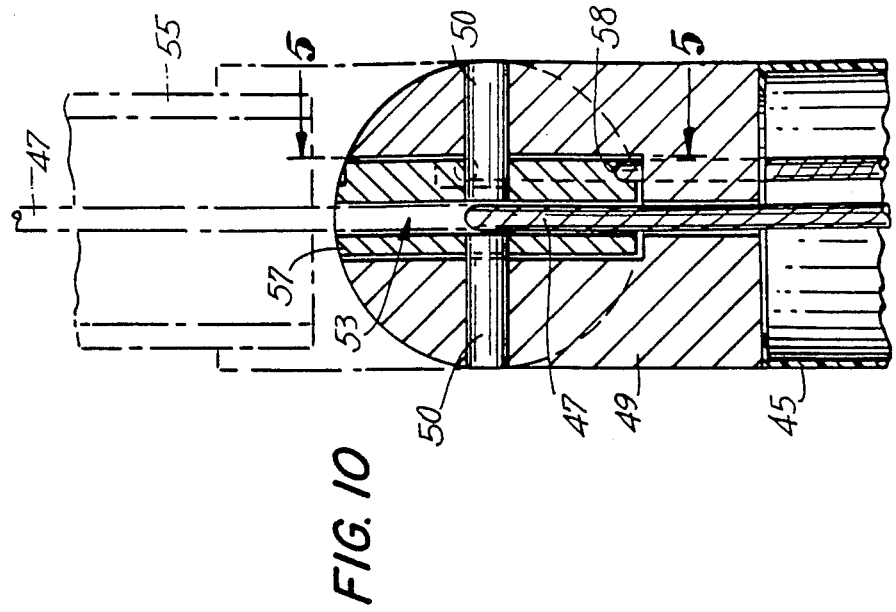
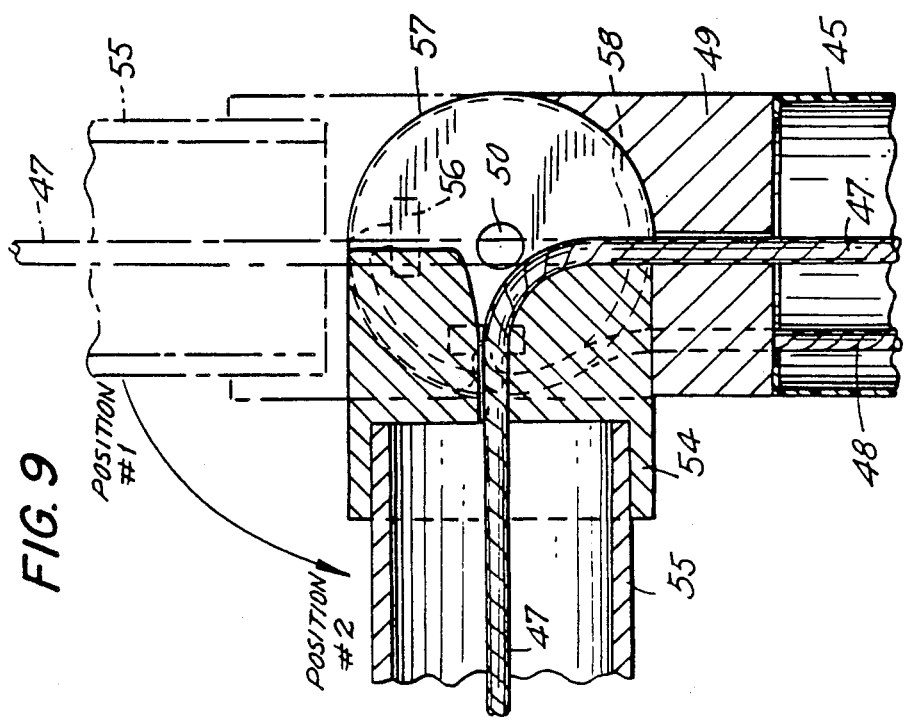

BIOPSY FORCEPS

TABLE OF CONTENTS 1.0 FIELD OF THE INVENTION
2.0 BACKGROUND OF THE INVENTION
3.0 SUMMARY OF THE INVENTION
4.0 BRIEF DESCRIPTION OF THE FIGURES
5.0 DETAILED DESCRIPTION

FIELD OF THE INVENTION

This invention relates to a biopsy forceps for use in a flexible fiberoptic medical instrument such as a bronchoscope. More particularly, this invention is directed to a biopsy forceps having an increased range of operability when used in conjunction with the flexible fiberoptic medical instrument such as a bronchoscope when obtaining tissue samples such as smooth growths in the trachea or main stem bronchii.

BACKGROUND OF THE INVENTION

From the turn of the century until the late 1960's, the only ways available to examine and take biopsy samples from a patient's lungs was either by surgery or through a rigid metal bronchoscope. In 1967, Ikeda, in Japan, introduced the first flexible fiberoptic bronchoscope (FFB). Over the last 20 years, as technological limitations and additional physician needs became evident, the FFB has undergone extensive revision and development.

Flexible Fiberoptic Bronchoscopy (FIG. 1, 10) is one of the most versatile tools available today in the evaluation of lung disease. Developed in the late 1960's, the Flexible Fiberoptic Bronchoscope (hereinafter equivalently referred to as FFB) enables Pulmonary Physicians to examine, under direct visualization, the oropharynx, vocal cords, trachea and main bronchial divisions of the bronchial tree. Through the Bronchoscope various biopsy tools, including brushes, forceps 27, and curettes may be passed to obtain samples of tissue from the visible airways and the pulmonary parenchyma. Diagnoses of cancer, tuberculosis and other infections, foreign body aspiration, airway obstruction and many other pulmonary disorders can be achieved relatively quickly, thoroughly and painlessly. Unlike rigid bronchoscopy or open lung biopsy, which must be done under general anesthesia, FFB is performed on an awake patient using local anesthesia, with proportionally less morbidity and mortality.

The procedure itself is relatively simple, and is usually done with the patient sedated, but awake. The Bronchoscope is passed either through the nose with the patient sitting, or through the mouth with the patient supine. As the scope is passed through the upper airway and the vocal cords, all visible sites are carefully examined, and biopsies are taken of any suspicious lesions. Upon entering the trachea, the methodical search is continued, of the trachea itself, the carina (the junction between the left and right lungs), the left and right main bronchii and all of the subsegments of both lungs. Next, under fluoroscopic guidance, lesions beyond the reach of the bronchoscope are located, biopsy tools are passed out into these lesions and samples are taken. Depending on the indication, it is also possible to wash out various parts of the lung and to send the fluid reclaimed for special diagnostic lab tests. After the examination is completed and all relevant specimens are obtained, the FFB is removed and the patient is observed, usually in hospital, for 12 to 24 hours for the development of complications. These are uncommon, and include persistent bleeding, pneumothorax (collapse of the lung on the side biopsied if the outer lining of the lung is unintentionally torn), or worsening of respiratory failure.

The entire procedure takes approximately 45 minutes, is painless and relatively easy in the hands of a skilled Bronchoscopist. It has rapidly become vital as a diagnostic and therapeutic tool, and has almost completely replaced other more invasive procedures in obtaining tissue samples in the majority of lung diseases.

A typical FFB 10 measures 790 mm in length and has two main parts; a working head 14 and an insertion tube 11. The working head contains the eyepiece 15, the ocular lens with a diopter adjusting ring 25, the attachments for the suction tubing 24 and suction valve 21 and for the cold halogen light source 16 and 18, and the access port, or "biopsy inlet" 19, through which various forceps, brushes and fluids can be passed into the suction/forceps channel 29 and out the distal end of the bronchoscope. This working head is attached to the second part, the insertion tube. This tube, on the average, measures 580 mm in length and has a diameter of 6.3 mm, and contains the fiberoptic bundles (which terminates in the objective lens 30 at the distal tip 12), the two light guides 31 and the suction/forceps channel 29. The distal end of the FFB has the ability to bend anterior and posterior only, the exact angle of deflection depending on the instrument used. A common range is from 160 degrees forward to 90 degrees backward, for a total of 250 degrees. The small bending radius is illustrated in FIGS. 3A and 3B as 13. The bending is controlled by the operator by adjusting the angle lock lever 22 and angulation lever 23 on the working head. However, unlike fiberoptic gastroscopes and colonoscopes, the bronchoscopic has no lateral deflection and, to direct it towards the right or the left, which is often necessary during certain procedures, (i.e. obtaining a biopsy sample), the entire instrument must be rotated by the operator.

Through the suction/forceps channel, many devices, such as biopsy forceps and brushes, can be passed through the length of the bronchoscope, exiting from its tip into a patients lungs, and are used to obtain samples. Brushes of different sizes, shapes and material (typically wire) can be passed into the airways of the lung, segments brushed and the sediment on the brush tip sent off to the laboratory for examination.

The typical biopsy forceps consists of a handle at one end connected to a long, flexible shaft 28 with an enhanced distal flexible segment and, at its distal end, two sharpened "cups" 27 (the forcep) which appose upon one another. When the ring at the handle end is pulled back, an inner wire or cable contained within the outer cable of the shaft slides backwards, opening the cups. Manipulating the FFB, the open forceps are then positioned (often with great difficulty since the bronchoscope has no lateral deflection), as close as possible to where one wants to obtain a sample, the ring is slid forward and the cups close. The forceps are then forcibly withdrawn, hopefully tearing off a small piece of the desired sample (i.e. tissue) of lung.

In a representative procedure, the patient is usually awake, although premedicated for sedation and drying of secretions, and is either sitting or supine. After local anesthesia is obtained by spraying Lidocaine on the nasal and oropharynx mucosa, the FFB is gradually passed through either the nose or the mouth into the posterior oropharynx, and positioned above the vocal cords. Additional Lidocaine is applied to the cords and throughout the rest of the procedure as the instrument is advanced. After careful examination of the cords and their movement, the FFB is advanced through them and is positioned in the trachea, which is also carefully anesthetized and examined. Any suspicious lesions or areas are biopsied and/or brushed. Then, in a planned, meticulous fashion, the remainder of the airways of the lungs are evaluated—from the carina, into all of the segments and accessible subsegments bilaterally and, if suspicious lesions, segments or anatomy are encountered, additional brushings and biopsies are taken. Next, under fluoroscopic guidance, brushes and forceps are advanced out beyond the range of direct vision of the FFB, into the peripheral lung, and additional samples of the lung parenchyma are removed. The biopsy sites are observed for bleeding, and, if necessary, adrenaline and saline washes are used to stop any major bleeding. If it is indicated, the FFB can also be wedged into one of the many subsegments of the lung and larger amounts of saline washed in and out, then evaluated in the laboratory for infection, malignancy, or other desired tests. After meticulous hemostasis is achieved, the FFB is withdrawn and the procedure is ended. Depending on the numbers of biopsies taken and the difficulty of the procedure, an average bronchoscopy takes from 30 minutes to an hour.

Over the last 20 years both the bronchoscope itself and ancillary tools like the biopsy forceps have undergone major, constant revision. There are many forceps commercially available today; ones with holes cut out of the cups; ones with jagged "alligator" jaws, designed for tearing off larger pieces of tissue; ones with needles jutting from between the cups, that are used to jab growths that are difficult to reach; and grasping forceps with interlocking teeth. There also exist double-jointed curettes which articulate only in an uncontrolled manner upon pressure to the extreme distal tip. The pressure is applied by forcing the entire biopsy forcep distal end against an internal obstruction. The distal end is realigned only by either forcing it against another obstruction, the walls of the trachea or by pulling it back into the biopsy channel. The double hinge is not otherwise controllable by the operator. This curette is clumsy and rarely used by practitioners.

Although all of these variations on the basic design of the forceps have their uses, there remains one very clear cut, specific dilemma that is encountered practically daily that no modification to date has yet been able to resolve.

The average internal diameter of the trachea in an adult man measures 12 mm, the right main bronchus 12-16 mm and the left main bronchus 11-14 mm. As noted above, the diameter of a representative bronchoscope measures 6.3 mm, occupying over half of the airway and leaving a very tight space to work within. The approach to lesions that arise directly ahead of the tip of the FFB is straightforward, and easily accessible without much manipulation of the bronchoscope.

However, it is very difficult, and often impossible, to take biopsies of smooth growths that arise off the walls of the trachea or of the main stem bronchii. The exit channel for the biopsy forcep is at the tip of the FFB, and the forceps itself can only be aimed by directing the FFB itself. As mentioned above, the tip of the FFB is only able to deflect in the anterior and posterior directions. Within the confines of the airways, the tip of the FFB is often only able to be flexed 30 to 40 degrees. In addition, looking down through the bronchoscope, the exit channel is placed at a "9:00" (on a clock, directly to the left, or west on a map) position and any tools passing through it come out from there. In order to sample lesions that arise off the right wall, the FFB must be rotated 180 degrees upon itself, and the operator is then essentially working upside down. This is a very difficult, clumsy position to maneuver in, may be additionally uncomfortable to the patient and often gives inadequate results.

Smooth lesions, and most mucosal growths are smooth, typically arise off the wall at an oblique angle, and the metal cups of the forceps slide off them, frustrating repeated attempts at taking biopsy specimens. In addition, mucosal growths are not fixed into position, therefore attempts made to stab them with the needle forceps only push them away. Unless the tip of the FFB can be flexed enough so that the lesion can be approached directly head on, (roughly approaching 90 degrees, which is essentially out of the designed range of the FFB) within these small work spaces, repeated attempts at sampling often end in failure.

It is also important to note that the biopsy channel of the FFB is a long, narrow channel. It is impossible to pass through it any device with a fixed angle built into its tip. Therefore, it has proven necessary to provide a device such as a Biopsy Forceps that is flexible enough to allow passage through the FFB.

Sometimes it is impossible to maneuver the FFB into the necessary position to obtain samples. If a tissue diagnosis cannot be made using Bronchoscopy, the patient must then undergo surgery to reach a definitive diagnosis.

It is therefore an object of the present invention to provide a biopsy forceps for use through a flexible fiberoptic bronchoscope, which would enable one to biopsy smooth growths that arise off the wall of the trachea or of the main stem bronchii easily and directly.

It is a further object of this invention that the biopsy forceps for removal of these smooth growths would be utilizable in a standard flexible fiberoptic bronchoscope and would enable the operator to obtain such biopsy samples without the need to orient himself in a cumbersome position.

3.0 SUMMARY OF THE INVENTION

The invention as disclosed and described herein is a biopsy forceps. Generally stated, the biopsy forcep of this invention comprises:

a. a flexible catheter having a distal and proximal end, said distal end being designed so as to be placed within a patients body to obtain a biopsy sample and said proximal end being designed so as to be located outside of said patients body and included means for controlling components of said biopsy catheter located at about the distal end of said flexible catheter;

b. a forcep cup assembly attached to the distal end of said flexible catheter;

c. a first hinge means attached to said flexible catheter placed proximally in relation to said forcep cup assembly, said first hinge means controlling the opening and closing of said forcep cup assembly;

d. a second hinge means attached to said flexible catheter placed proximally in relation to said first hinge means and said forcep cup assembly, said second hinge means controlling the articulation of the portion of said flexible catheter including said forcep cup assembly and first hinge means, said second hinge means and resultant articulation being controllable from the proximal end of said flexible catheter.

More specifically, this invention comprises a biopsy forceps for use with a flexible fiberoptic medical instrument such as a bronchoscope. The biopsy forceps of this invention has an increased degree of flexibility by virtue of a hinge means which enables the forceps cups or assembly at the distal end of the shaft to pivot at an angle and in a fashion hereto for impossible away from the longitudinal axis of the forceps shaft. The biopsy forceps of this invention are used through a flexible fiberoptic bronchoscope of which the distal portion comprises a narrow, flexible metal shaft with the biopsy forceps cup assembly positioned at its far or distal end. The proximal portion consists of the plastic handle and hinge angle control.

The flexible shaft of the forcep is preferably comprised of a coiled, spring-like flexible cable. Running through its hollow core are two smooth, solid metal wires that slide back and forth within the cable. One of the wires ends at and controls the opening and closing of the biopsy cups. When the wire is pushed forward, the biopsy cups open; when pulled back, they close.

In this invention, immediately proximal to the distal part of the forceps containing the cup mechanism is a small hinge contiguous with the walls of the flexible cable to which the biopsy handle is attached. This hinge is freely movable, allowing the distal end of the forceps to now rotate back and forth away from the longitudinal axis of the flexible cable in relation this hinge or more specifically the proximal portion of this hinge.

Within the flexible shaft or catheter is an additional thin wire of flexible, smooth metal (the "angle control wire") which runs parallel to the wire which controls the biopsy cups. At the distal end, this angle wire connects to the hinge on one side of the cup mechanism. Pulling on this angle wire will pull the portion of the hinge in which the cup mechanism is seated in a circular or arc type motion in relation to the other, proximal portion of the hinge. This rotation occurs about a pivot pin which is disposed on the hinge and which joins the proximal and distal portion of the hinge.

In this invention, at the proximal end the angle wire enters the plastic handle and joins a hinge control means. A tab element on this control protrudes through the handle and can only move forwards and backwards. When pushed all the way away from the operator, it rests at zero degrees, the home position, and the distal tip of the forceps containing the cup mechanism will be straight or parallel and in-line with the longitudinal axis of the proximal portion of the angle hinge. When the operator pulls this Tab backwards, the distal biopsy cup mechanism pivots to that exact degree indicated from the longitudinal axis of the proximal portion of the angle hinge, and will remain there until the operator decides to change it. Since the wire controlling the biopsy cups is flexible, it can bend into any angle, and the cups will open and close as they normally do when fixed at any desired angle. The angling hinge is, therefore, entirely separated from the coexisting mechanism for opening and closing the cups, in no way interferes with that separate operation and enables greater versatility in the positioning of the biopsy cups.

4.0 BRIEF DESCRIPTION OF THE FIGURES

Figure 1:
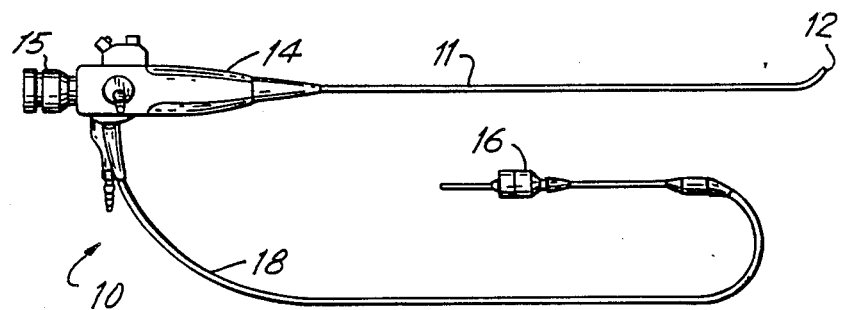
FIG. 1 shows the flexible fiberoptic bronchoscope including the control body, insertion tube, eye piece, distal end and light guide cable.
Figure 2:
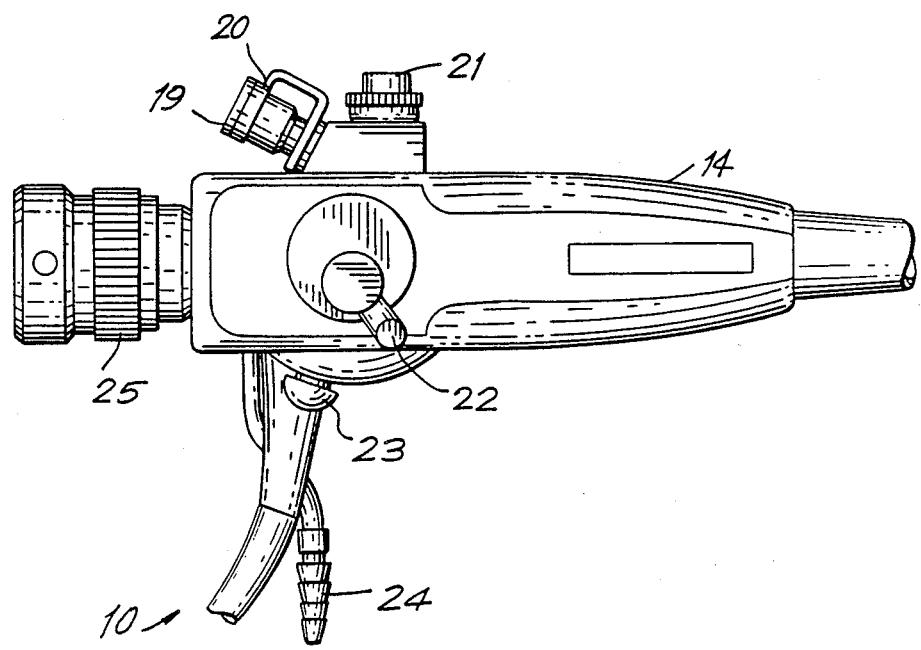
FIG. 2 shows the control body of FIG. 1 in greater detail including the inlet for insertion of biopsy forceps.
Figure 3A:
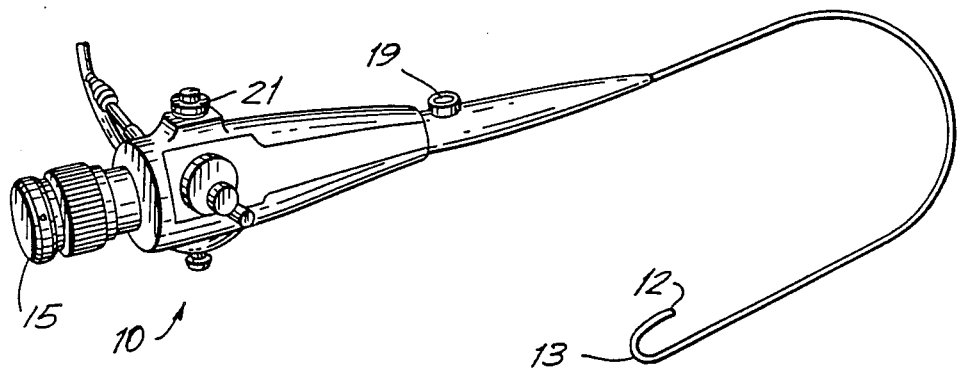
Figure 3B:
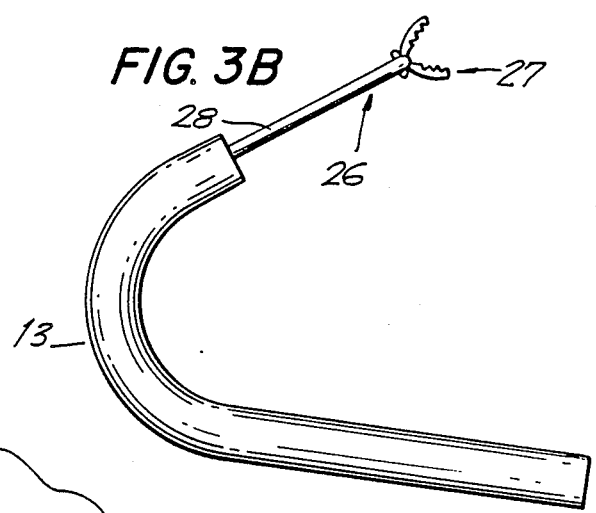

FIG. 3-(A) illustrates the small bending radius of a standard flexible fiberoptic bronchoscope; (B) illustrates a prior art type of biopsy forcep merging and in position for taking a sample from a curved portion from the bent distal end of the bronchoscope.

Figure 4:
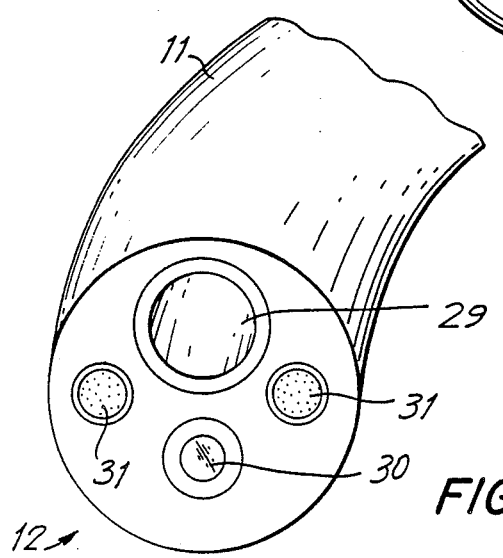

FIG. 4 is an enlarged view of the distal end of the fiberoptic bronchoscope illustrating the channel through which the biopsy forcep is passed;

FIG. 5 illustrates a double-hinged biopsy forcep structure including both the distal and proximal end;

FIG. 6 is an illustration of the distal or cup end of the double-hinged biopsy forcep being inclined at a 90° angle from the longitudinal access of the biopsy forcep flexible shaft.

Figure 7A:
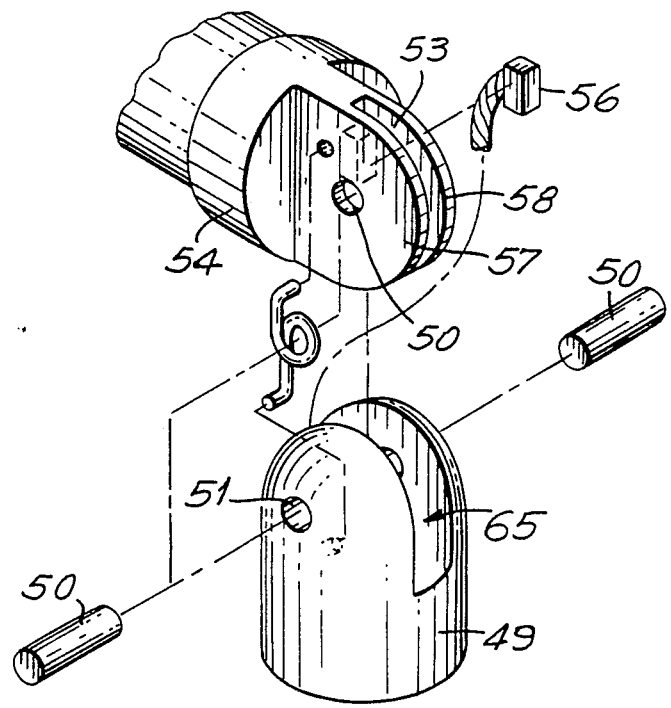
Figure 8A:
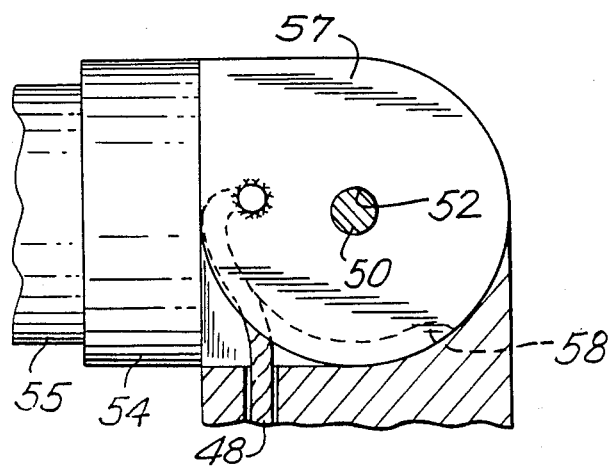
Figure 11:
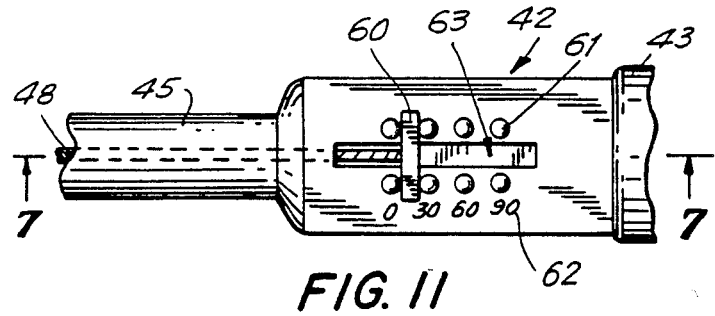
Figure 12:
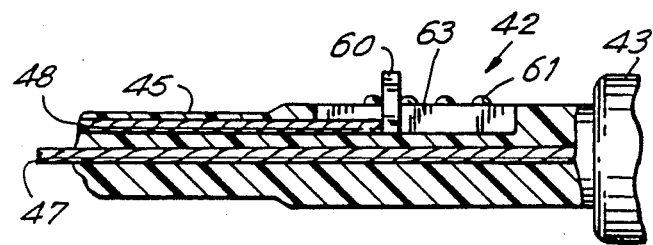

FIG. 7 is an exploded view of the double-hinged biopsy forcep of FIG. 6 including the portion of the hinge mechanism adjacent to the biopsy forcep cups; the pivot pin portion; the portion of the hinge mechanism adjacent to the handle or proximal end of the biopsy forcep structure and the cables which control the cups and the hinge mechanism;

FIG. 7A is an exploded view of the double-hinged biopsy forcep of FIG. 6 including the portion of the hinge mechanism adjacent to the biopsy forcep cups; the pivot pin portion; the portion of the hinge mechanism adjacent to the handle or proximal end of the biopsy forcep structure; the cables which control the cups and the hinge mechanism and including integral spring means mounted between flat portions of elements 49 and 54 which are parallel when the forcep cup assembly is aligned with the longitudinal axis of the catheter;

FIG. 8 is a side view of hinge mechanism when said hinge has rotated the biopsy cups to a 90° angle to the longitudinal axis of the biopsy forcep shaft;

FIG. 8A is a side view of the hinge mechanism when said hinge has rotated the biopsy cups to a 90° angle to the longitudinal axis of the biopsy forcep shaft, showing a weld connecting the wire 48 with the second hinge means;

FIG. 9 is a side illustration (Position #2) of the angle hinge articulated to a perpendicular (90°) angle to the axis of the biopsy forcep shaft along with a view of the biopsy cup control cable in relation to said hinge mechanism and a dashed line view of the position of the hinge (Position #1), hinge angle control cable and anchor and cup control wire when said hinge is aligned with the longitudinal axis of the biopsy forcep flexible shaft;

FIG. 10 is an end view of FIG. 9 looking towards the biopsy cups from said hinge mechanism in Position #2 which illustrates the relationship and positioning of the hinge control cable and the biopsy cup control cable;

FIG. 11 is a front perspective view of the proximal or handle end of the double-hinged biopsy forcep including the hinge-angle control slide;

FIG. 12 is a side cut-away view along axis 7 of FIG. 11 of the proximal or handle end of the double-hinged biopsy forcep with a hinge angle control slid or Tab.

5.0 DETAILED DESCRIPTION

In a specific embodiment of this invention, the biopsy forceps which is to be used in a bronchoscope comprises a flexible catheter terminating in a distal and proximal end, defining an interior cavity there between, a forcep cup assembly at said distal end and a forcep controller at said proximal end; said catheter surrounding a first and second wire;

said first wire traversing the inside of the entire length of said catheter;

said first wire attached at its distal end a first hinge means;

said first hinge means being connected to said forcep cup assembly;

said first wire attached at its proximal end to a first control means on said forcep controller, whereby moving said first control means on said forcep controller acts to operate said first hinge means selectively opening or closing said forcep cup assembly;

said second wire traversing the entire length of the interior cavity of said flexible catheter;

said second wire attached at its distal end to a second hinge means;

said second hinge means being connected to said forcep assembly including said first hinge means;

said second wire being attached at its proximal end to a second control means on said forcep controller, whereby moving said second means on said forcep controller acts to operate said second hinge means thereby articulating said forcep cup assembly towards or away from longitudinal axis of the proximal portion of said second hinge means.

It is preferred that the shaft of the forcep or catheter comprised a coil spring-like flexible outer cable and that the wires (first and second) inside of the interior cavity this catheter can freely slide back and forth. The first wire within the catheter are used to control both the opening and closing of the forcep cups or assembly to perform the actual biopsy sampling the second wire is used to control the angle of deflection away from the longitudinal axis of the proximal portion of the second hinge means catheter. Depending upon the movement of the angle wire (also called the second wire) controlling the deflection of the forcep assembly, the movement may cover a range from 0°–120°. A further description of this invention is provided in the description which follows.

More specifically, the biopsy forceps 40 of this invention for use through a flexible fiberoptic bronchoscope is shown in FIG. 5. It measures preferably about 128 cm in length, of which the distal portion (114 cm) comprises a narrow, flexible metal shaft 45 (which also is contained with the bronchoscope channel 29, FIG. 4) with the biopsy forceps cups 46 positioned at its far or distal end. The proximal portion (preferably about 14 cm long) consists of the plastic handle 44 and hinge angle control 42.

The flexible shaft 45 of the forcep is preferably comprised of a coiled, spring-like flexible cable. Running through its hollow core are the smooth, solid metal wires 47 and 48 that slide back and forth within the cable. The distal end of cable 47 ends at and controls the opening and closing of the biopsy cups 46. The inner solid metal wire 47 is attached to two hinges 59 when the cup assembly, which then cross and become the cups 46 themselves. When the wire 47 is pushed forward, the cups 46 open; when pulled back, they close.

The plastic handle 44 is located at the proximal end and is located on the bronchoscope control handle. The Cable 45 joins the handle at its lower end, and the inner wire 47 runs up through the handle and is attached to a sliding outer plastic grip 43 that fits over the handle. The preferred proximal handle 44 contains a grip ring 64 for the operators finger. By sliding the outer plastic piece or grip 43 forwards over the handle 44, the metal wire 47 is pushed forwards, opening the cups 46 at the distal end in the manner indicated by the "A" arrows on FIG. 6. Likewise, pulling back on the outer plastic piece or grip 43 closes the cups 46.

Until this invention, typical biopsy forceps (see FIG. 3B—26) were only able to open and close, leaving its placement maneuvering entirely dependent on the positioning of the entire bronchoscope unit 10. The invention herein, however, tremendously increases the versatility of the forceps, allowing them to be positioned at even the most difficult angles to reach lesions.

In a preferred embodiment of this invention, immediately proximal to the distal part of the forceps containing the cup mechanism 46 is a small hinge 41 so as to be contiguous with the walls of the flexible cable 45 to which the biopsy handle 44 is attached. This hinge is freely movable, allowing the distal end to now rotate back and forth away from the longitudinal axis of the flexible cable 45.

Within the flexible cable 45, is an additional thin wire 48 of flexible, smooth metal (the "angle control wire") that runs parallel to the inner wire 47 which controls the biopsy cups 46. This angle wire 48 is preferably no more than about 0.5 mm diameter thick, or if semicircular or flat, no more than about 0.5 mm thick, and preferably does not make the forceps shaft larger, enabling it fit within the size constraints and other limitations of the biopsy channel 29 of existing FFBs. At the distal end, this metal angle wire connects to the hinge 41 in the cable and is attached to on side of the cup mechanism. Pulling on this angle wire will pull the portion of the hinge 59 in which the cup mechanism is seated down in a circular or arc type motion (Arrow B, FIG. 6). This rotation occurs on pivot pin 50 (axis 4, FIG. 6) which is disposed within pivot pin holes 51 and 52 on the hinge 41 at axis 4 on FIG. 6. Preferably, one pivot pin 50 extends from one side of the outer surface 49 of the hinge to the other side, and is flush with the surface 49. Pushing on the angle wire 48 will push the portion of the hinge 59 in which the cup mechanism is seated up in a circular motion (Arrow C, FIG. 6) in the direction of rotating on the same pivot pin 50.

In a preferred embodiment of this invention, at the proximal end the angle wire 48 enters the plastic handle and joins a new control, the hinge control 42. The Tab 60 element of this control protrudes through the handle 44 and through slot 63 on the side, and can only move forwards and backwards. When pushed all the way away from the operator, it rests at zero degrees, the home position, and the distal tip of the forceps containing the cup mechanism will be straight or parallel and in-line with the longitudinal axis of the proximal portion of said second or angle hinge 49. Preferably, on the outside of the handle are raised "bumps" 61, with numbers or indicia 62 next to them indicating the angle in degrees that the tip can be rotated (0, 30, 60, 90). Sliding this Tab lever 60 backwards seats it between two sets of parallel raised bumps and keeps it positioned there. When the operator pulls this Tab backwards, the distal cup mechanism including elements 46, 54 and 55 pivots to that exact degree indicated from the longitudinal axis of the proximal portion of said angle hinge 49, and will remain there until the operator decides to change it. Since the core wire 47 controlling the cups 46 is flexible, it can bend into any angle, and the cups will open and close as they normally do when fixed at any desired angle. The angling hinge 41 is entirely separated from the coexisting mechanism for opening and closing the biopsy cups and in no way interferes with that separate operation.

It is very straight forward to use this new forceps. The bronchoscope 10 is positioned just above the site that the operator wants to sample, straight ahead in the most comfortable location. The biopsy forceps 40 is then passed into the Biopsy inlet 19 or through the Rubber Inlet seal 20 through the forceps channel 29 and the cups 46 positioned at the spot to be sampled. Next, by pulling up on the hinge angle control Tab 60 that arises off the side of the handle 44, the angle wire 48 pulls the distal cup mechanism including elements 46, 54 and 55, and rotates it into the desired angle of approach, usually head on or at right angle at 90° degrees. The Tab 60 is kept in position by the raised bumps 61. Using the FFB, the forceps are placed against the lesion, the cups opened and a sample is taken when the cups are closed against or around a portion of the lesion. The hinge angle control Tab 60 is then pushed forwards (towards the distal end or biopsy cups) into the straight position (home position), thereby straightening the distal tip of the forceps into alignment with the longitudinal axis of the proximal portion of said angle hinge 49 and also possibly flexible shaft 45 and thereby allowing it to be pulled out through the FFB channel 29 and 11.

It is, therefore, now possible to take samples from any tracheal or bronchial lesion no matter how awkward the approach would be using standard biopsy forceps. By passing the forceps described herein through the channel 29 aligned so that the distal tip may then be rotated towards the site that one wants, the operator can leave the FFB in place and just use the forceps for positioning. Being much smaller and more versatile, the biopsy forceps will increase the yield and decrease the time required for this ubiquitous problem.

In the preferred embodiment the angle hinge 41 is comprised of essentially three components. The first component is the portion 54 of the angle hinge which is closest to the distal end of the biopsy forcep apparatus or cups 46. The second portion 49 of the angle hinge, which integrally fits over the first portion in a straddle-like fashion, is adjacent to and is connected to and joint at 66 the flexible shaft cable 45. The third element of the angle hinge pin is a pivot pin 50 which connects the other two elements together through an opening 51 and 52 which traverses the center of these components. The angle hinge pin 50 also serves as the central pivot point along axis 4 (FIG. 6) for the angle hinge 41. It is also within the scope of this invention that the angle hinge pin 50 be provided with a integral spring means which spring would act to provide a retaining force for the biopsy forceps to remain along the same longitudinal axis as the shaft cable. It is also envisioned that the spring means may be separate from the angle pin and may be attached between and to both portions 54 and 49 of the angle hinge. In this fashion the spring means would serve the same function see FIG. 7A.

In all the embodiments both portions 54 and 49 are provided with a channel 53 and 65 respectively, through their central interior through which channel the cable 47 which controls the cups 46 would pass. On portion 54 the channel 53 is formed by and is located in between two rounded flanges 57 on which are formed the pivot pin holes 52. In addition, on one of the flanges is formed a circular cable pulley slot 58 which extends outward width-wise from said flange 57, which slot engages the hinge angle control wire 48. The distal end of wire 48 ends with an anchor block 56 which is preferably inserted into a similar shaped opening 67 formed on said flange 57. Any movement of wire 48 would pull on anchor block 56 thereby causing rotation of the hinge 41 about axis 4. It is prevented from being removed from the chamber 67 by virtue of the other portion of the hinge preventing its movement out laterally and the channel being narrower than the width of the distal end of the cable creating a slot channel block fit. In another embodiment, it is envisioned that the end of wire 48 may also be directly attached to the flange 57 by welding (see FIG. 8A) or some other similar means which would secure the end to the flange and enable rotation about the pivot axis. In addition, the cable 48 which controls the articulation of the angle hinge would also pass through the channel 65 of hinge portion 49 adjacent to the shaft cable.

In a preferred embodiment the angle hinge 41 is of a cylindrical shape so as to conform with the shape and internal diameter of the shaft cable and the biopsy forcep apparatus 45. In addition, it may pass through the bronchoscope 10 and patient without providing any additional obstruction. The cable or wire means 48 for articulating the angle hinge is preferably a stainless steel or other material of high tensile strength and of relatively high rigidity.

In the operation of this device, a force pulling on the angle cable 48 causes the hinge to articulate in a direction away from the longitudinal axis of the shaft cable 45. In this fashion the portion of the angle hinge adjacent to the biopsy forceps may be articulated up to 90° from the longitudinal axis of the shaft cable. It is further envisioned that the biopsy forceps may be returned to their original position along the longitudinal axis of the shaft cable 45 by pushing the angle cable back to its original position from the biopsy forcep control means 42 on the outside of the bronchoscope. This may be used alone to return it to its original position or in conjunction with the spring means discussed above.

Aspects of the present invention are not to be limited in scope by the preferred embodiment described herein, since this embodiment is intended as a single illustration. Indeed it is also within the scope of this invention that the biopsy catheter described herein, by varying the size and or diameter of the cable and forceps, is useful with laryngoscopes, gastroscopes, sigmoidoscopes or colonoscopes. Therefore, various modifications of the invention in addition to those shown and described herein will become apparent to those skilled in the art from the foregoing description and accompanying drawings.

I claim:

1. A biopsy forcep comprising:
   a. a flexible catheter having a distal and proximal end, said distal end being designed so as to be placed within a patient's body to obtain a biopsy sample and said proximal end being designed so as to be located outside of said patient's body and including means for controlling components of said biopsy catheter located at about the distal end of said flexible catheter;

b. a forcep cup assembly attached to the distal end of said flexible catheter;

c. a first hinge means attached to said flexible catheter placed proximally in relation to said forcep cup assembly, said first hinge means controlling the opening and closing of said forcep cup assembly and;

d. a second hinge means attached to said flexible catheter placed proximally in relation to said first hinge means and said forcep cup assembly, said second hinge means controlling the articulation of the portion of said biopsy forcep including said forcep cup assembly and first hinge means, said second hinge means and resultant articulation being controllable from the proximal end of said flexible catheter.

2. The biopsy forcep of claim 1 wherein said second hinge means comprises a distal hinge portion adjacent to said forcep cup assembly and a proximal hinge portion adjacent said flexible catheter.

3. The biopsy forcep of claim 1 wherein said first hinge means includes means for operating when said second hinge means has articulated said forcep cup assembly away from longitudinal axis alignment with said second hinge means.

4. The biopsy forcep of claim 1 wherein said second hinge means includes means for enabling said forcep assembly to articulate at axis least about 90 perpendicular to the longitudinal access of said flexible catheter at the portion of said flexible catheter adjacent and proximal to said second hinge means.

5. The biopsy forcep of claim 4 said second hinge means further comprising a cylindrical shape.

6. The biopsy forcep of claim 1 including a cable attached to said second hinge means, wherein the articulation of said distal end of flexible catheter is provided by movement of said cable pulled in a direction toward the proximal end of said flexible catheter.

7. A biopsy forcep comprising:
flexible catheter terminating in a distal and proximal end, defining an interior cavity therebetween, a forcep cup assembly located at said distal end and a forcep controller at said proximal end, said catheter surrounding a first and second wire;
said first wire traversing the entire length of the interior cavity of said catheter;
said first wire being attached at its distal end to a first hinge means;
said first hinge means being connected to said forcep cup assembly;
said first wire being attached at its proximal end to a first control means on said forcep controller, whereby moving said first control means on said forcep controller acts to operate said first hinge means thereby opening or closing said forcep cup assembly; and
said second wire traversing the entire length of the interior cavity of said flexible catheter;
said second wire attached at its distal end to a second hinge means;
said second hinge means being connected between said first hinge means and said flexible catheter;
said second wire being attached at its proximal end to a second control means on said forcep controller, whereby moving said second control means on said forcep controller acts to operate said second hinge means thereby articulating said forcep cup assembly towards or away from the longitudinal axis of the proximal portion of said second hinge means.

8. The biopsy forcep of claim 7 wherein said first hinge means includes means for operating when said second hinge means has articulated said forcep cup assembly away from the longitudinal axis of said proximal portion of said second hinge means.

9. The biopsy forcep of claim 7 wherein said second hinge means includes means for enabling said forcep assembly to articulate at least about 90° perpendicular to the longitudinal axis of said flexible catheter at the portion of said flexible catheter adjacent and proximal to said second hinge means.

10. The biopsy forcep of claim 7 wherein said second hinge means comprises a distal hinge portion adjacent to said forcep cup assembly and a proximal hinge portion adjacent said flexible catheter.

11. The biopsy forcep of claim 10 said second hinge means further comprising a cylindrical shape having said proximal hinge portion of said second hinge means being attached to said flexible catheter and said distal hinge portion of said second hinge means having a rounded hemispherical shape, a slot traversing the diameter of said proximal hinge portion to accommodate said distal hinge portion and an opening formed on opposite sides of a wall of said proximal hinge portion which opening traverses the diameter of said proximal hinge portion from outer surface to outer surface and which opening aligns in size and location with openings formed on said distal hinge portion when said distal hinge portion is brought into association with said proximal hinge portion to form said second hinge means and a pivot pin means for joining said proximal and said distal hinge portions.

12. The biopsy forcep of claim 11 wherein said second hinge means further comprises an interior cavity defined by walls of said proximal and distal portion hinge portions.

13. The biopsy forcep of claim 11 wherein said second wire traverses through said second hinge means and connects onto said first hinge means.

14. The biopsy forcep of claim 11 wherein the articulation of said distal hinge portion adjacent to said biopsy forceps is provided by movement of the second wire being pulled in a direction toward the proximal end of said flexible catheter.

15. The biopsy forcep of claim 11 wherein said second hinge means is tensioned by a spring means whereby said spring means provides a force to enable said second hinge means to return to a position in line with the longitudinal axis of said proximal portion of said second hinge means after said second said flexible catheter.

16. The biopsy forcep of claim 15 spring means is attached between the portion of said proximal hinge portion adjacent to said flexible catheter and the distal hinge portion.

17. The biopsy forcep of claim 16 wherein said second wire is attached to said second hinge means.

18. The biopsy forcep of claim 17 wherein said attachment is a weld.

19. The biopsy forcep of claim 11 wherein said first wire traverses through said distal hinge portion and proximal hinge portion to said first hinge means..

20. The biopsy forcep of claim 7 wherein said second hinge means is defined by cylindrical shaped walls of about the same diameter as said flexible catheter.

21. The biopsy forcep of claim 17 wherein said attachment is by means of a slot channel block fit.

22. The biopsy forcep of claim 7 wherein said biopsy forcep in combination with flexible fiberoptic bronchoscope.

23. The biopsy forcep of claim 7 wherein said second control means further comprises a tab attached to said proximal end of said second wire.

24. The biopsy forcep of claim 23 wherein said tab protrudes from a slot formed on said forcep controller, said tab overlapping the outer edges of said slot and engaging means for securing said tab and said second wire at a particular location on said forcep controller whereby said second hinge may be retained at a particular angle in relation to the distal end of said biopsy forcep.

* * * * *